United States Patent [19]

Turtiainen

[11] Patent Number: 5,483,414

[45] Date of Patent: Jan. 9, 1996

[54] ELECTRICAL IMPEDANCE DETECTOR FOR MEASUREMENT OF PHYSICAL QUANTITIES, IN PARTICULAR OF TEMPERATURE

[75] Inventor: Heikki Turtiainen, Vantaa, Finland

[73] Assignee: Vaisala Oy, Vantaa, Finland

[21] Appl. No.: 40,129

[22] Filed: Mar. 30, 1993

[30] Foreign Application Priority Data

Apr. 1, 1992 [FI] Finland ..................................... 921449

[51] Int. Cl.⁶ ............................... H01G 7/00; H01G 5/01
[52] U.S. Cl. ......................... 361/282; 361/278; 361/280; 374/163
[58] Field of Search .................................... 361/278, 282, 361/281, 277, 280, 286; 374/163, 184; 338/25; 324/71.1, 105

[56] References Cited

U.S. PATENT DOCUMENTS

| | | | |
|---|---|---|---|
| 2,639,247 | 5/1953 | Squier | 174/124 R |
| 3,210,607 | 10/1961 | Flanagan | 361/330 |
| 3,443,293 | 5/1969 | Masujima | 29/25.42 |
| 3,649,891 | 3/1972 | Lawless | 361/282 |
| 3,854,112 | 12/1974 | Greenwood | 338/47 |
| 4,921,328 | 5/1990 | Seth | 350/96.34 |

FOREIGN PATENT DOCUMENTS 1386200  5/1975  United Kingdom.
2158229  6/1985  United Kingdom.

OTHER PUBLICATIONS

W. N. Lawless, "A Low Temperature Glass–Ceramic Capacitance Thermometer", The Review of Scientific Instruments, vol. 42, No. 5, May 1971.

Masashi Onishi et al., "Properties of Bi–Pb–Sr–Ca–Cu–O Glass–Ceramic Fibers Formed by Glass–Drawing Method", Japanese Journal of Applied Physics, vol. 30, No. 6A, Jun., 1991, pp. L988–L990.

"Proceedings Sensor 91 Congress", Part A/B, 13 May 1991, Band 1, vol. 1, pp. 237–246.

S. G. Bishop and W. J. Moore, "Chalcogenide Glass Bolometers", Applied Optics, vol. 12, No. 1, Jan. 1973, pp. 80–83.

*Primary Examiner*—Bot L. Ledynh
*Attorney, Agent, or Firm*—Jones & Askew

[57] ABSTRACT

Electrical impedance detector for measurement of physical quantities, in particular of temperature. The detector comprises electrodes (11,14), between which the electrical impedance (C;R) that represents the physical quantity to be measured is measured. Between these electrodes (11,14) there is an active material whose impedance properties are a function of the physical quantity to be measured. The active material of the detector is a very thin thread-like glass or glass-ceramic fibre (10), which has been manufactured by means of the glass-drawing technique. Further, a process for the manufacture of said detectors is described.

10 Claims, 5 Drawing Sheets

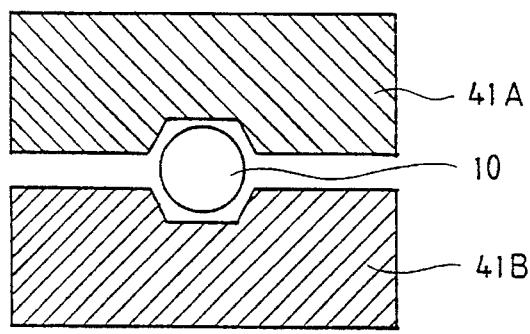
FIG. 8A
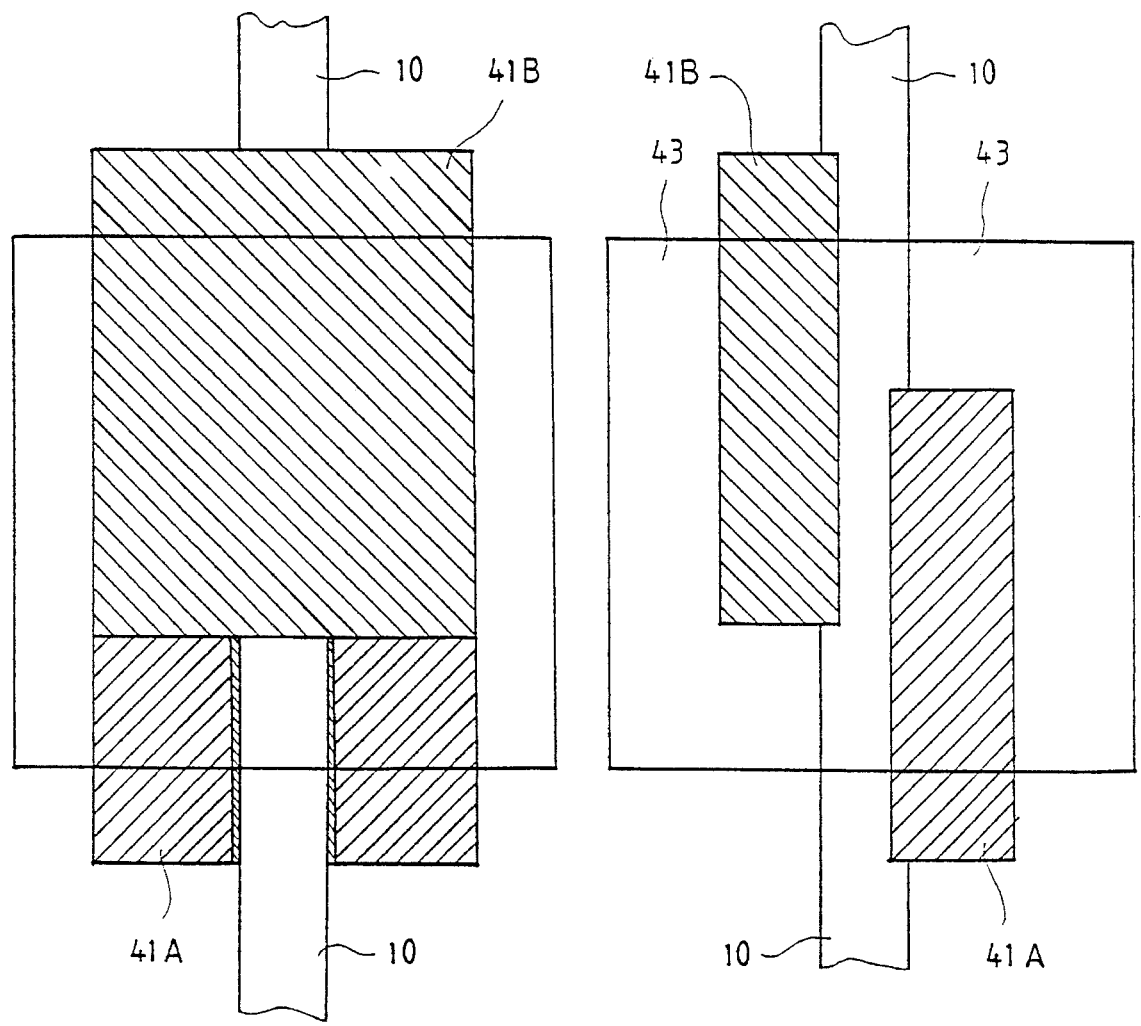
FIG. 8B
FIG. 8C

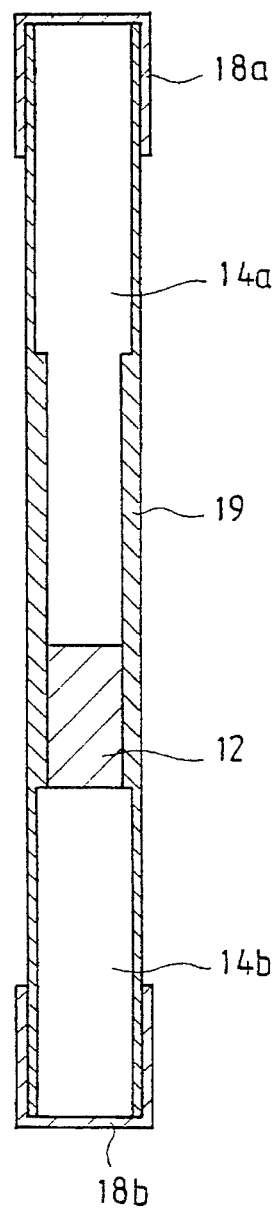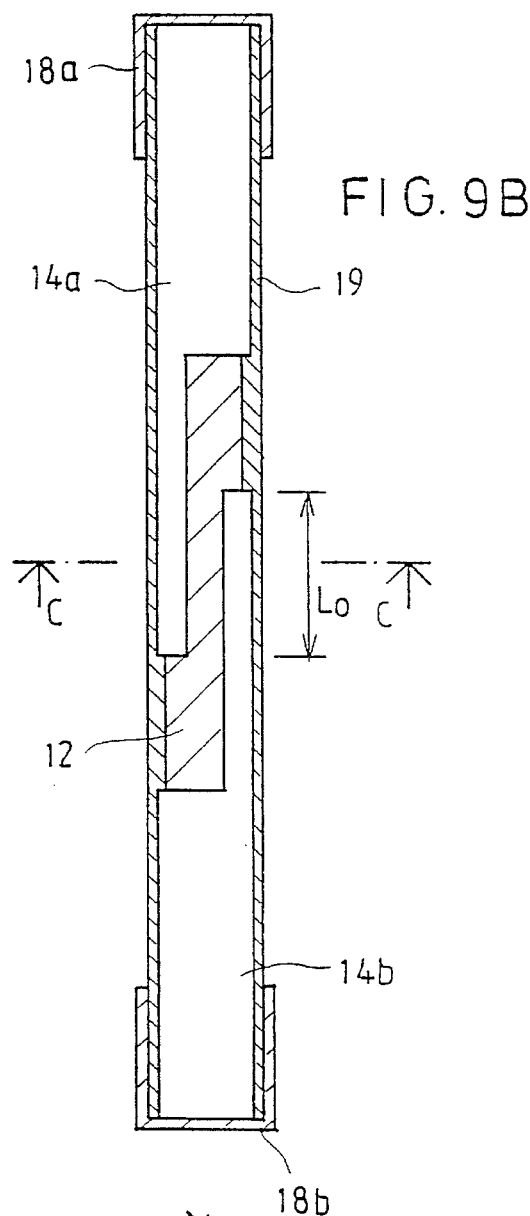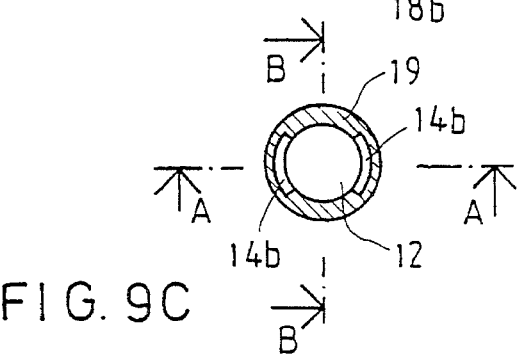

ELECTRICAL IMPEDANCE DETECTOR FOR MEASUREMENT OF PHYSICAL QUANTITIES, IN PARTICULAR OF TEMPERATURE

The invention concerns an electrical impedance detector for measurement of physical quantities, in particular of temperature, which detector comprises electrodes, between which the electrical impedance that represents the physical quantity to be measured is measured, and between which electrodes there is an active material whose impedance properties are a function of the physical quantity to be measured.

Further, the invention concerns a process for manufacture of electrical impedance detectors, said detector being intended for measurement of physical quantities, in particular of temperature or relative humidity.

In a number of applications, high speed, small size, and low radiation error are required from measurement detectors, in particular from detectors intended for measurement of temperature. Said requirements are particularly strict, e.g., in temperature detectors of radiosondes. In many applications, corresponding properties are also required from detectors used for measurement of relative humidity.

As is known in prior art, for example, as temperature detectors of radiosondes, as a rule, capacitive detectors are used, whose active material is a ceramic whose dielectricity is dependent on the temperature. The prior-art glass-ceramic temperature detectors are, however, of relatively large size, and therefore their speed and radiation error would require some improvement. The radiation error produced by solar radiation has been the most important problem in the temperature measurement by radiosondes with the use of prior-art temperature detectors.

Besides capacitive detectors, in radiosondes and equivalent, resistive temperature detectors and thermoelements have also been used.

In prior art, capacitive humidity detectors are known in whose capacitance the dielectric material used is a polymer, a ceramic, or a glass-ceramic, whose dielectric constant is a function of the humidity absorbed by it. The speed and corresponding properties of these detectors also require development, in particular in view of radiosonde applications.

The processes of manufacture of the prior-art impedance detectors and equivalent have been complicated, sometimes difficult to make automatic and difficult to apply to automatic processes of manufacture.

It is known in prior art that the dielectricity of certain glasses or glass-ceramic materials is dependent on the temperature. In this respect and with respect to the prior art related to the present invention, reference is made to the papers:

(1) The Review of Scientific Instruments Volume 42, Number 5, May 1971 W. N. Lawless: "A Low Temperature Glass-Ceramic Capacitance Thermometer"

(2) Japanese Journal of Applied Physics Vol. 30, No. 6A, June 1991, pp. L 988 . . . L 990 Masashi Onishi, Michihisa Kyoto, and Minoru Watanabe "Properties of Bi—Pb—Sr—Ca—Cu—O Glass-Ceramic Fibres Formed by Glass-Drawing Method"

(3) Proceedings Sensor 91 Congress 19.—16. May 1991 Nürnberg, Vol. IV, pp 237 . . . 246 Th. Hübert, U. Banach: "Glaskeramiken für Kapazitive Sensoren zur Messung von Temperatur und Feuchte"

(4) Applied Optics, Vol. 12, No. 1/Jan. 1973, pp. 80 . . . 83: S. G. Bishop and W. J. Moore: "Chalcogenide Glass Bolometers"

In the paper (2) cited above, properties of superconductivity of glass-ceramic fibres produced by the glass-drawing method are dealt with. In the present invention, where applicable, the glass-drawing methods and glass raw-materials suggested in said paper can be employed. In the paper (3) mentioned above, a humidity detector based on a glass-ceramic is described.

With respect to the prior art related to the invention, reference is made additionally to the U.S. Pat. No. 3,649,891, wherein a capacitive temperature detector is described in particular for measurement of cryogenic temperatures ($T \approx 1 \ldots 20°K.$). In the cited patent, the dielectric material of the detector capacitance is the compound strontium-titanate, $SrTiO_3$, which has been crystallized in a glass matrix under control. Said capacitive detector is particularly well suitable for measurement of cryogenic temperatures, because the dielectric constant of its glass-ceramic material is lowered steeply and evenly as the temperature is lowered in said temperature range. In said US patent, the construction of the detector capacitance is, however, of quite a large size and even otherwise conventional, so that, owing to its low speed and to its radiation error, it is not suitable for a temperature detector, e.g., for radiosondes or equivalent.

The object of the present invention is further development of the prior-art electrical-impedance detectors and of the processes for their manufacture, in particular in respect of the temperature detectors, so that the drawbacks discussed above can be substantially avoided.

It is a further object of the invention to provide a process for the manufacture of said impedance detectors, by whose means it is possible to manufacture said detectors at a favourable unit cost and with uniform quality and properties of the detectors.

It is a particular object of the invention to provide an impedance detector whose size is small and whose mass is low, in which case the detector has a high speed and a low radiation error.

In relation to the above, an object of the invention to provide a novel impedance detector suitable in particular for a temperature detector for radiosondes, the principle of operation of said detector being either resistive or capacitive.

In view of achieving the objectives stated above and those that will come out later, the detector in accordance with the invention is mainly characterized in that the active material of the detector is a very thin thread-like glass or glass-ceramic fibre which has been manufactured by means of the glass-drawing technique.

On the other hand, the process in accordance with the invention for the manufacture of a detector is mainly characterized in that the process comprises a combination of the following steps:

a continuous detector-fibre thread of substantially circular section is manufactured by means of a glass-drawing technique in itself known out of a molten glass mix which has been alloyed with an additive or with additives that provide(s) the active material of the detector with suitable electrical properties, that said detector-fibre thread is crystallized by means of heat treatment into a glass-ceramic form or its material is chosen or otherwise treated so that an active detector material is produced whose capacitance and/or resistance depend on the temperature or, in particular cases, on the amount of water absorbed by the active material, that, for individual detectors, said detector-fibre thread is cut-off into suitable pieces of detector-fibre thread, which are provided with terminals, and/or to which terminals are connected, and/or to whose electrodes, which have been provided at the thread-drawing stage, terminals are coupled or connected, between which terminals the impedance of the detector can be measured.

The detectors of the invention are manufactured out of a detector-fibre thread, which has been made by the glass-drawing technique as a continuous process, preferably, for example, by making use of the so-called double-crucible process. The drawing of the detector-fibre thread takes place in the glass form. If a glass-ceramic is used as the active material, hereupon the active layer of the detector is crystallized into the glass-ceramic form so that a material is produced whose dielectricity and/or resistance depends on the temperature of the active material.

Thus, the detectors in accordance with the invention are made of continuous detector thread of circular section whose material or some component in the material is a substance whose dielectric constant or resistivity depend on the physical quantity to be measured, as a rule, on the temperature.

In some exceptional cases, by means of the process of the invention, it is also possible to manufacture an impedance detector for relative humidity, in which case the dielectric constant of the active glass-ceramic material has been arranged to be dependent on the amount of water absorbed by the material.

According to a provisional estimate, the most advantageous form of application of the invention is a capacitive temperature detector, which is intended for radiosonde use and whose capacitance is typically in a range of C=3 ... 10 pF when the temperature T to be measured varies in a range of T=−90° C. ... +45° C.

Out of a continuous detector thread made by means of the glass-drawing technique, as a rule, pieces of about 1 ... 5 cm are cut-off, which pieces are either provided with a central electrode in the thread-drawing process, to which the electrodes are attached, and/or onto the outer face of which fibre thread suitable conductor patterns are made, e.g., by a photolithographic method, in order that it should also be possible to make a continuous detector thread in a continuous process.

In the following, the invention will be described in detail with reference to some exemplifying embodiments of the invention illustrated in the figures in the accompanying drawing, the invention being in no way strictly confined to the details of said embodiments.

FIG. 5A is, at the same time, a sectional view taken along the line A—A, and FIG. 5B a sectional view taken along the line B—B, in FIG. 5C.

FIGS. 8A, 8B and 8C illustrate masks used in exposures of the photoresist taking place from four different directions.

FIGS. 9A and 9B are axial sectional views perpendicular to one another of the construction of a capacitive humidity detector manufactured by the method as illustrated in FIGS. 6 to 8. FIG. 9A is, at the same time, a sectional view taken along the line A—A in FIG. 9C, and FIG. 9B a sectional view along the line B—B in FIG. 9C.

FIG. 9C is a sectional view taken along the line C—C in FIG. 9B.

Figures 5A, 5B:
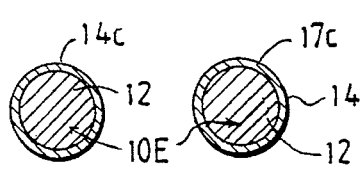
FIGS. 5A and 5B are cross-sectional views of a resistive temperature detector in accordance with the invention.
Figure 5C:
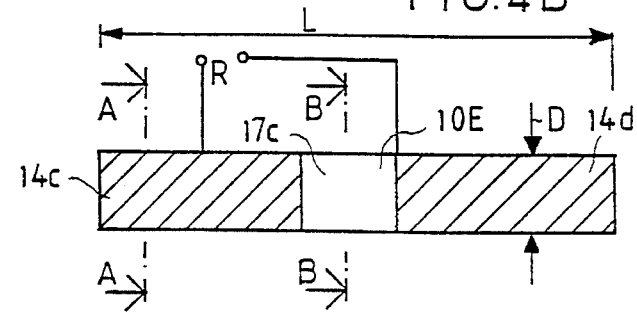
FIG. 5C is a side view of the detector shown in FIGS. 5A and 5B.
Figure 6C:
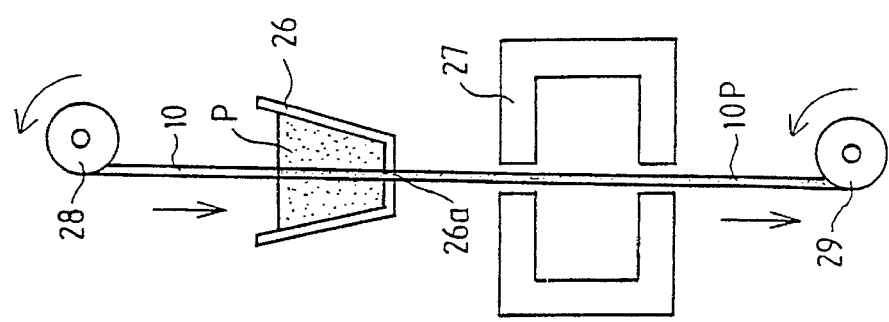
FIG. 6C is a schematic illustration of the method by which the glass-ceramic fibre manufactured in the way illustrated in FIG. 6A is coated with a conductive material.
Figure 6B:
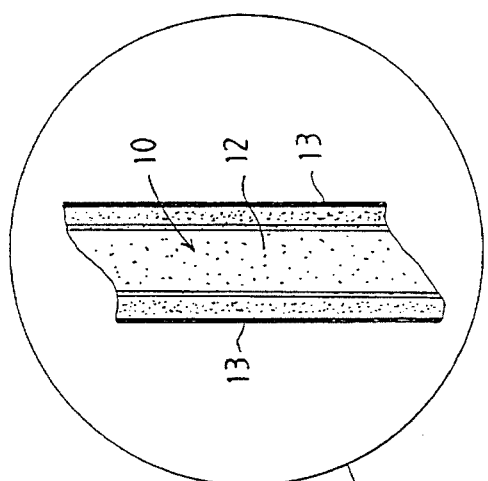
FIG. 6B is an enlarged central axial sectional view of a glass-ceramic fibre in accordance with the invention, which has been manufactured by means of a nozzle as shown in FIG. 6A.

FIGS. 1 to 4 illustrate some preferred capacitive or resistive temperature detectors in accordance with the invention. FIGS. 5A, 5B and 5C illustrate a resistive temperature detector in accordance with the invention. FIGS. 6 to 8 are schematic illustrations of a preferred process in accordance with the invention for the manufacture of said detectors, and FIGS. 9 illustrate a capacitive temperature detector manufactured by means of said process.

Figure 1:
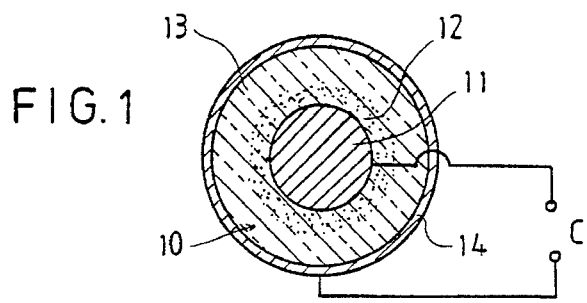
FIG. 1 is a cross-sectional view of a capacitive temperature-detector fibre in accordance with the invention.

According to FIG. 1, the capacitive temperature detector is composed of a threadlike, very thin glass fibre 10 of circular section, in which there is a central electrode 11 of a metal, e.g. platinum, and a glass-ceramic annular layer 12 around it. On the glass-ceramic layer 12, there is a hermetic annular glass layer 13, and on it a conductive electrode layer 14, so that the structure is coaxial. The capacitance C to be measured is formed between the electrodes 11 and 14. The dielectric of this capacitance C consists of the layers 12 and 13 connected in series, of which layers the glass-ceramic layer is, e.g., barium-strontium-titanate, $Ba_xSr_{1-x}TiO_3$. The dielectric constant of this glass-ceramic and of other, corresponding glass-ceramics depends on the temperature. The hermetic glass layer 13 that surrounds the glass-ceramic prevents access of moisture into the active material of the dielectric layer 12.

Glass-ceramic materials absorb moisture, which affects their dielectric constant and, thus, produces an error in the measurement of temperature. This phenomenon can be utilized in a capacitive measurement detector for relative humidity. According to the process of the invention, out of a continuous detector fibre as shown in FIG. 1, pieces of a length of about 1 ... 5 cm, preferably about 2 cm, are cut-off. The detector fibre 10 is very thin, and its outer diameter D is preferably in a range of D=25 ... 500 μm. For example, in a 2 cm long detector, the capacitance measured between its electrodes 11 and 14 at a temperature T=20° C. is C≈5 pF. When the temperature T varies in a range of T=−90° C. ... +45° C., the capacitance varies in a range of C=3 ... 10 pF, and the detector capacitance C is increased substantially linearly when the temperature T detectable by the detector rises.

Figure 2A:
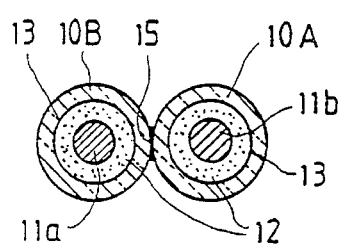
FIG. 2A is a cross-sectional view of a capacitive temperature-detector made of two glass-ceramic fibres that have been joined together.
Figure 2B:
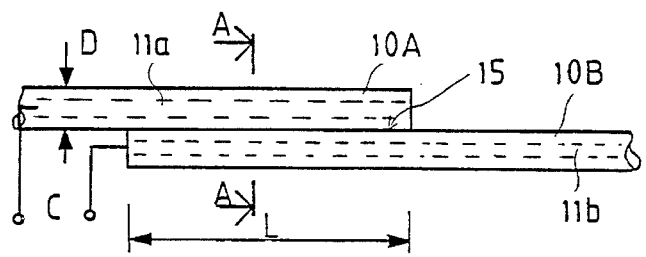
FIG. 2B is a side view of the detector shown in FIG. 2A, FIG. 2A being, at the same time, a sectional view taken along the line A—A in FIG. 2B.

The capacitive temperature detector shown in FIGS. 2A and 2B consists of two detector fibres 10A and 10B, which have been joined together along their length L, e.g., by means of an adhesive joint 15. The capacitance C is formed, and it is measured between the central electrodes 11a and 11b. The range of the detector capacitance C can be adjusted by changing the dimension L. The dimension L is, as a rule, L<5 cm while the outer diameter D of the fibres 10A and 10B is, as a rule, in a range of D=25 ... 500 μm. In a detector construction as shown in FIGS. 2A and 2B, it is, as a rule, an advantage that no outer electrode 14 is needed at all, as it is needed in FIG. 1.

Figure 3A:
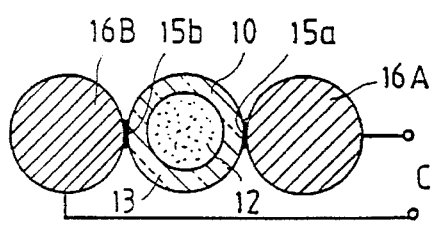
FIG. 3A shows a capacitive temperature detector in accordance with the invention which is made of a piece of glass-ceramic fibre.
Figure 3B:
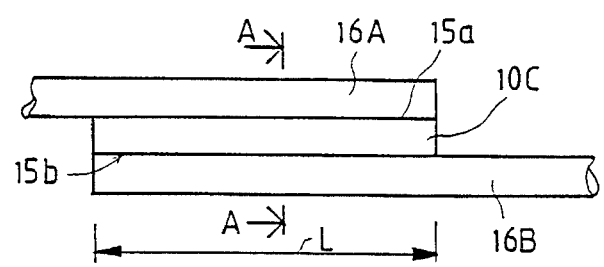
FIG. 3B is a side view of the detector shown in FIG. 3A, FIG. 3A being a sectional view taken along the line A—A in FIG. 3B.

The detector shown in FIGS. 3A and 3B is composed of a piece of detector fibre 10C. In this detector fibre, there is no metallic central electrode 11, but its volume is occupied completely by a glass-ceramic inner fibre 12, on which there is a hermetic shield layer 13 of glass. Onto said layer 13, by means of the joints 15a and 15b, metallic electrode wires 16A and 16B have been attached over the length L, the detector capacitance C being measured between said electrode wires.

Figure 4A:
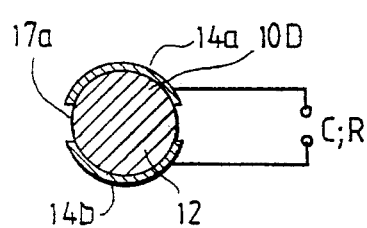
FIG. 4A is a cross-sectional view of a capacitive or resistive detector in accordance with the invention.
Figure 4B:
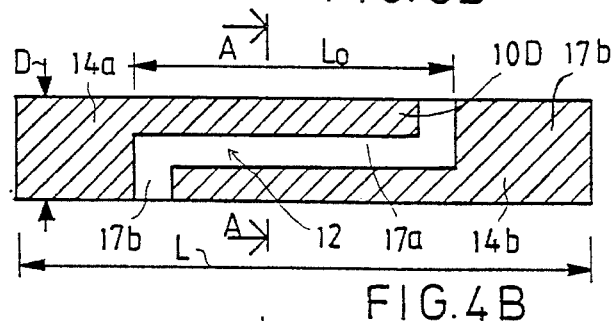
FIG. 4B is a side view of the detector shown in FIG. 4A, FIG. 4A being a sectional view taken along the line A—A in FIG. 4B.

The detector as shown in FIGS. 4A and 4B consists of a piece 10D of detector fibre of a length L, onto which piece 10D conductor patterns 14a and 14b have been applied. Between these patterns, there are axial insulation gaps 17a and radial insulation gaps 17b, which separate the conductor patterns 14a and 14b from one another. The construction shown in FIGS. 4A and 4B can be used either as a resistive temperature detector, as a humidity detector, or as a slightly modified capacitive detector.

When a construction as shown in FIGS. 4A,4B is used as a humidity detector, the glass-ceramic 12 is a material whose dielectric constant depends on the humidity absorbed by the material. Humidity has access to the material 12 through the intermediate areas 17a and 17b and, if necessary, also through the conductor patterns placed within the length $L_0$, which patterns can be made so thin that they are penetrable to humidity but are, however, still electrically conductive. When a construction as shown in FIGS. 4A and 4B is used as a resistive humidity detector, the material 12 is a glass-ceramic whose resistance depends on the temperature. When the construction in FIGS. 4A and 4B is used as a capacitive detector, a hermetic layer 13 as shown in FIG. 3A is placed around the glass-ceramic 12, the conductor patterns 14a and 14b being applied onto said layer 13. The resistance R or capacitance C of the detector is measured between the conductor patterns 14a and 14b.

In FIGS. 5A,5B,5C, a resistive temperature detector in accordance with the invention is illustrated, wherein conductor patterns 14c and 14d have been applied onto a glass-ceramic fibre 10E, which patterns 14c and 14d are separated from one another by an insulation gap 17c. The resistivity of the glass-ceramic material 12 depends on the temperature. The resistance R of the detector is, at the room temperature, of an order of 10 kΩ, and, at the temperature of −90° C., of an order of 1 MΩ. The resistance is measured between the conductor patterns 14c and 14d.

In the following, with reference to FIGS. 6, 7 and 8, a preferred process in accordance with the invention for the manufacture of a detector, in particular of a capacitive temperature detector, will be described. In the process, in a number of respects, it is possible to use devices and process steps similar to those used in the prior-art processes and devices for the manufacture of optical fibres. It should be emphasized that, in the following, just one preferred process of manufacture is described, and that the processes included in the scope of the present invention may differ even substantially from said process.

In the invention, it is also possible to use a material to which some such component has been added whose dielectric constant depends on the physical quantity to be measured.

Figure 6A:
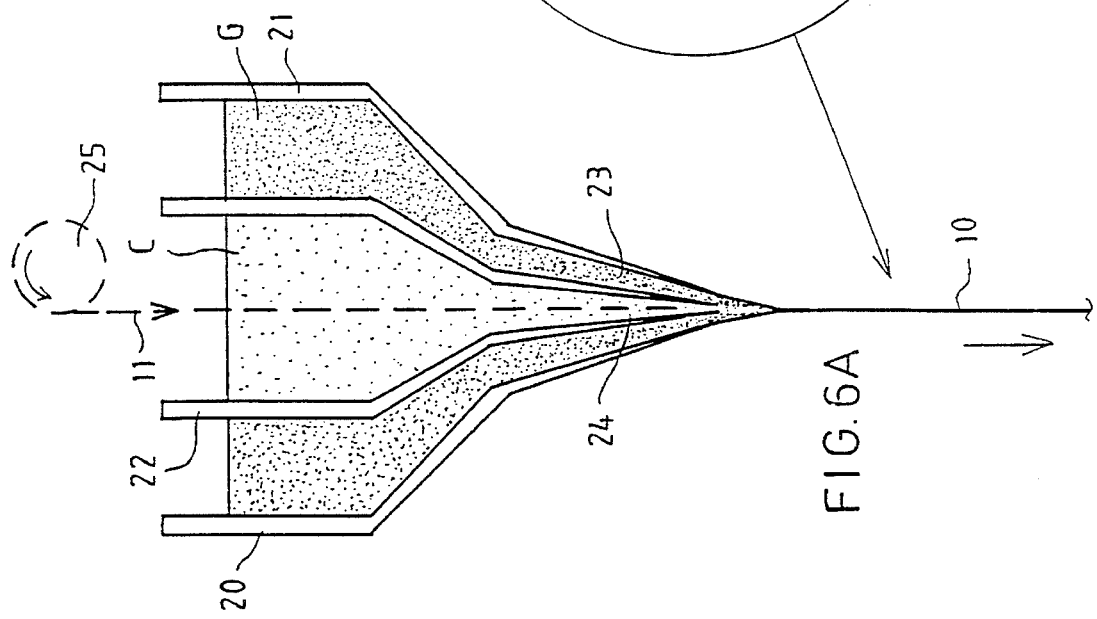
FIG. 6A illustrates a double crucible used in the manufacture of the glass fibre in accordance with the invention and of the nozzle arrangement in its bottom.
Figure 7:
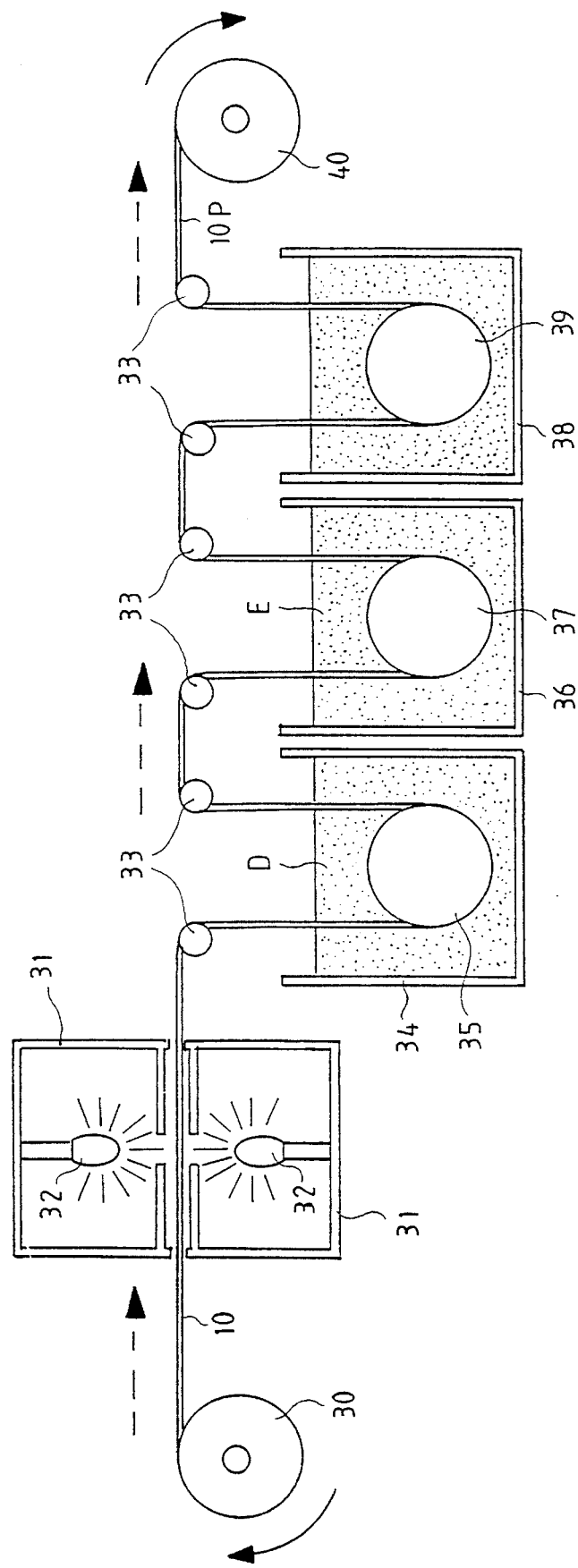
FIG. 7 illustrates the exposure of a fibre coated with a photoresist in the way illustrated in FIG. 6C, the processing of the resist, the etching, and the dissolving as a continuous process.

According to FIG. 6A, the drawing of the detector-fibre thread 10 takes place by using the so-called double-crucible process, which is in itself known from the manufacture of optical fibres. In this process, a crucible-nozzle device 20 is used, which comprises two crucibles placed one inside the other, viz. an outer crucible 21 and an inner crucible 22. In the bottom of the outer crucible 21, there is an annular nozzle 23, and inside said nozzle, there is an inner nozzle 24 opened into the bottom of the inner crucible 22. The outer crucible 21 contains glass material G, for example aluminosilicate-glass in a molten state, and the inner crucible 22 contains molten core glass C.

Examples of active materials suitable for a capacitive detector:

a) aluminosilicate-glass-based material

The core glass C is made of a mixture of barium, strontium, titanium, silicon, and aluminium oxides. An example of the alloying proportion:

| | |
|---|---|
| BaO: | 5% |
| SrO: | 30% |
| $TiO_2$: | 35% |
| $SiO_2$: | 20% |
| $Al_2O_3$: | 10% |

By means of the ratio of the barium and Sr oxides, it is possible to affect the shape of the temperature-dependence curve of the dielectricity. The composition given above is suitable for a sonde application. When the fibre 10 is drawn, the fibre cools rapidly, in which case it remains in the glass-like (amorphous) form. In the heat treatment, the fibre is heated (for example) at 1100° C. for 2 h, whereby a glass-ceramic material is produced, in which there are barium-titanate and strontium-titanate crystals in a glass matrix.

b) aluminoborate-based material

The composition is the same as above, except that all of the silicon oxide has been substituted for by boric oxide $B_2O_3$. In such a case, the heat treatment is, for example, 1 h at 850° C.

Active materials suitable for a resistive detector are, for example, chalcogenide glasses, which are semiconductors and can be drawn to a fibre. In literature, the chalcogenide glass $Ti_2SeAs_2Te_3$ has been used in bolometer applications (cited paper (4)). Thus, this material is a glass, not a glass-ceramic.

When the fibre thread 10 is drawn, it cools rapidly, whereby both the surface layer 13 and the core layer 12 remain in the glass form. An essential step in the invention is the heat treatment applied to the fibre thread after it has been drawn, in which treatment strontium-titanate and barium-titanate crystals are formed in the core glass part 12. By means of the temperature profile and maximum temperature of the heat treatment, it is possible to affect the crystal size, and thereby it is possible to control and to set the dielectric properties and the temperature-dependence of the fibre thread. The heat treatment of crystallization requires quite a long time, so that it should be preferably applied to a fibre placed on a reel, preferably so that, after a batch of fibre has been drawn, the whole reel is placed in the heat-treatment oven.

FIG. 6B is an axial sectional view of a fibre thread 10, which comprises the core part 12 described above and the surface layer 13. In the glass-drawing process, the fibre thread 10 becomes circular by nature. As regards the heat treatment mentioned above, which is essential in the present invention, reference is made to the cited papers (1) and (3) mentioned above initially as well as to the concentrations of doping agents given in them.

In connection with the drawing process of the fibre thread 10 described above, as an alternative embodiment, it is possible to feed an electrode wire 11 from a wire reel 25 into the fibre (illustrated by the dashed line in FIG. 6A), in which case a fibre thread 10A and 10B similar to that shown in FIGS. 2A and 2B is produced, which thread differs from that shown in FIG. 6B. As an alternative, an inner electrode can be placed in the interior of the fibre by placing a metal rod inside a glass-tube blank and by pulling the metal rod and the glass tube together into a fibre, or by first producing a hollow fibre and then metallizing its inside afterwards. In the latter case, the structure of the fibre thread is, in the other respects, similar to that shown in FIG. 1, except that, in stead of a solid central electrode 11, there is a hollow tubular central electrode. The latter construction, which is hollow in the interior, is in some applications advantageous in the respect that, through the central hole in the glass fibre 10, the transfer of heat becomes more efficient and, thereby, the operation of the detector becomes more rapid and the response times become shorter.

After the crystallization of the core part 12 of the glass fibre 10 described above, the fibre thread 10 is coated with a suitable paste. This is carried out, e.g., by means of a process as shown in FIG. 6C. The glass-fibre thread 10 to be coated, for example, as shown in FIG. 6B, is passed from its starting reel 28 into a crucible 26 and through the hole 26a placed in its bottom further through a sintering furnace 27. The crucible 26 contains a suitable coating paste P. After the sintering furnace 27, the fibre 10P, whose cross-section becomes, e.g., similar to that shown in FIG. 1, runs onto the receiving reel 29. The process illustrated in FIG. 6C is a coating process in itself known and commonly used in the coating of optical fibres. In stead of paste coating and sintering, it is possible to use other coating processes in themselves known, such as vapour deposition.

The electrodes and electrode patterns applied onto the glass-fibre thread 10, such as the electrode 14 shown in FIG. 1, the electrodes 14a and 14b shown in FIGS. 4A and 4B, and the electrodes 14a,14b,14c, and 14d shown in FIGS. 5A,5B,5C and 9A,9B, 9C, are prepared, e.g., by means of the photolithographic method illustrated schematically in FIG. 7. In this method, the fibre 10 is coated by means of a crucible 26 with a hole in its bottom, described above in relation to FIG. 6C. Hereupon the coated glass-fibre thread 10 is fed from the starting reel 30 through the exposure units 31, to whose sources of light 32 certain areas in the photoresist are exposed. After the exposure units 31, the fibre 10 is fed over the guide rolls 33 and over the drum 35 in the developing tank 34, in which the resist is processed by means of the developer chemicals D. The fibre thread 10 is passed further over the drum 37 in the etching tank 36, in which the exposed areas are etched by means of the etching chemicals E, whereupon the fibre thread 10 is passed over the guide rolls 33 further over the drum 39 in the dissolving tank 38, where the chemicals F dissolve the resist off. Hereupon the fibre 10P is reeled onto the receiving reel 40. According to FIG. 7, the process from the exposure to the removal of the resist takes place as a continuous process.

FIGS. 8A, 8B and 8C illustrate the stage of exposure of the fibre 10 in three illustrations perpendicular to one another. The exposure takes place in a particular precisely aligned jig 41A and 41B from four different directions. The exposure masks 42a and 42b have been prepared, e.g., by etching suitable grooves into silicon, a corresponding technique being employed in prior art in the preparation of joints of optical-fibre cables. The reference numeral 43 denotes the areas to be exposed.

By means of the steps described above, onto the outer faces of the electrodes applied onto the fibre thread, a glass layer 19 impervious to water (FIGS. 9A,9B,9C) is formed, e.g., by means of glass paste. In such a case, the coating process is, e.g., similar to the coating process described in relation to FIG. 6C and carried out with a conductive paste.

By means of the process steps described above, a continuous detector-fibre thread 10 can be produced simply and economically. The next step in the manufacture of the detectors in accordance with the invention is the cutting-off of this fibre thread into pieces for individual detectors, the axial length L of said pieces being, as a rule, in a range of L=1 . . . 5 cm, preferably L≈2 cm. Hereupon, contact areas 18a and 18b suitable for soldering are prepared to the ends of the detectors, which areas are shown in FIGS. 9A and 9B.

Thus, in FIGS. 9A, 9B and 9C, a capacitive detector is shown, which has been manufactured by means of a process as illustrated above in FIGS. 6 to 8 and which is in the other respects similar to that illustrated above in FIGS. 4A and 4B, except that the detector is coated with an insulation layer 19 impervious to water, such as a glass paste. The active area of the detector shown in FIGS. 9 is placed over its length $L_0$, at which the capacitance C to be measured is formed, the dielectric of said capacitance C being the glass-ceramic core material 12 described above, whose dielectric constant is a function of the temperature. The capacitance C of the detector is measured between the electrodes 18a and 18b.

In the following, the patent claims will be given, and the various details of the invention may show variation within the inventive idea defined in said claims and differ from what has been stated above for the sake of example only.

I claim:

1. Electrical impedance detector for measurement of physical quantities, in particular of temperature, which detector comprises electrodes (11, 14), between which the electrical impedance (C;R) that represents the physical quantity to be measured is measured, and between which electrodes (11, 14) there is an active material whose impedance properties are a function of the physical quantity to be measured, characterized in that the active material of the detector is a very thin thread-like glass-ceramic fibre (10) which has been manufactured by means of the glass-drawing technique.

2. Detector as claimed in claim 1, characterized in that said fibre is a glass-ceramic fibre (10) whose drawing into a glass-fibre thread has been carried out in a glass-like form and whose crystallization into the glass-ceramic form has been carried out in a heat treatment.

3. A detector as claimed in claim 1 and intended for measuring resistance or capacitance, characterized in that, in the glass-ceramic material, the active constituent is a crystalline barium-strontium titanate, $Ba_xSr_{1-x}TiO_3$, wherein x is in a range of 0 . . . 1, which is present in a glass matrix.

4. A detector as claimed in claim 1 and intended for measuring resistance or capacitance, characterized in that the glass-ceramic fibre (10) is surrounded by a hermetic glass layer (13), which prevents access of moisture into the material of the active dielectric layer (12).

5. A detector as claimed in claim 1 and intended for measuring resistance or capacitance, characterized in that the detector-fibre thread is of substantially circular cross-section, and that the diameter of the detector-fibre thread (10) is of an order of D=25 . . . 500 μm.

6. A detector as claimed in claim 1 and intended for measuring resistance or capacitance, characterized in that the detector is coaxial and comprises a solid central electrode wire (11) or a corresponding hollow electrode thread and a glass-ceramic layer (12) placed around said central electrode, on which layer (12) there is a hermetic glass layer (13) and on the glass layer an electrode layer (14) and/or electrode patterns (14a, 14b, 14c, 14d).

7. A detector as claimed in claim 1, characterized in that the detector comprises two detector-fibre threads (10A, 10B), which are joined together as parallel to one another by means of a joint (15) over the certain length (L) of the threads, on which length a detector capacitance (C) is formed that can be measured between the central electrodes (11a, 11b) placed inside the detector-fibre threads (10A, 10B).

8. A detector as claimed in claim 1, characterized in that the detector comprises a piece of detector-fibre thread (10C) with no central electrode, electrode wires (16A, 16B) parallel to said piece of thread (10C) being attached to both sides of said piece of thread (10C), between which electrode wires (16A, 16B) the detector capacitance (C) can be measured.

9. A or resistive detector as claimed in claim 1, characterized in that, onto a piece of glass-ceramic-fibre thread (10D) with no central electrode, electrode patterns (4a, 4b) have been applied, which are placed as at least partly overlapping each other in the axial direction while separated from one another by an insulation gap (17a, 17b), and that the detector capacitance or resistance (C;R) is measured between said conductive outer electrodes (14a, 14b).

10. A detector as claimed in claim 1, characterized in that, onto a glass-ceramic thread (10E) whose resistance is a function of the temperature, conductor patterns (14c, 14d) have been applied, which are separated from each other axially by an insulation gap (17c).

\* \* \* \* \*